United States Patent [19]
Middendorf et al.

[11] Patent Number: 5,346,603
[45] Date of Patent: Sep. 13, 1994

[54] DNA SEQUENCING

[75] Inventors: Lyle R. Middendorf; John A. Brumbaugh, both of Lincoln, Nebr.

[73] Assignee: The Board of Regents of the University of Nebraska, Lincoln, Nebr.

[21] Appl. No.: 950,734

[22] Filed: Sep. 24, 1992

Related U.S. Application Data

[60] Continuation of Ser. No. 799,712, Nov. 26, 1991, abandoned, which is a continuation of Ser. No. 632,605, Dec. 24, 1990, abandoned, which is a continuation of Ser. No. 78,279, Jul. 27, 1987, abandoned, which is a division of Ser. No. 594,676, Mar. 29, 1984, Pat. No. 4,729,947.

[51] Int. Cl.$^5$ ............................................. C25B 9/00
[52] U.S. Cl. .............................. 204/299 R; 204/180.1; 204/182.8
[58] Field of Search .............. 204/180.1, 182.8, 299 R

[56] References Cited

U.S. PATENT DOCUMENTS

| | | | |
|---|---|---|---|
| 3,640,813 | 2/1972 | Nerenberg | 204/182.8 X |
| 3,980,546 | 9/1976 | Caccavo | 204/182.8 X |
| 4,111,785 | 9/1978 | Roskam | 204/182.8 X |
| 4,284,491 | 8/1981 | Vesterberg | 204/299 R |
| 4,431,506 | 2/1984 | Gorman, Jr. et al. | 204/182.8 X |
| 4,689,295 | 8/1987 | Taber et al. | 435/6 |

Primary Examiner—John Niebling
Assistant Examiner—C. Delacroix-Muirhe
Attorney, Agent, or Firm—Vincent L. Carney

[57] ABSTRACT

To sequence long strands of DNA, cloned strands having lengths longer than 100 bases are, in one embodiment, marked on one end with biotih. These strands are divided into 4 aliquots and each aliquot: (1) is uniquely chemically treated to randomly terminate the strands at the non-biotinylated end at a selected type of base; and (2) is moved continuously by electrophoresis through a different one of four identical channels. In the one embodiment, the strands are randomly terminated at a selected base type and they are moved into avidin, which due to high affinity, combines with the biotin marked ends of shorter strands before the longer strands are fully resolved in the gel. The avidin is marked with fluorescein, the strands are scanned and the signals are decoded. In another embodiment, the strands are synthesized, with termination at a selected base type and marked either by the above method or by ethidium bromide.

6 Claims, 6 Drawing Sheets

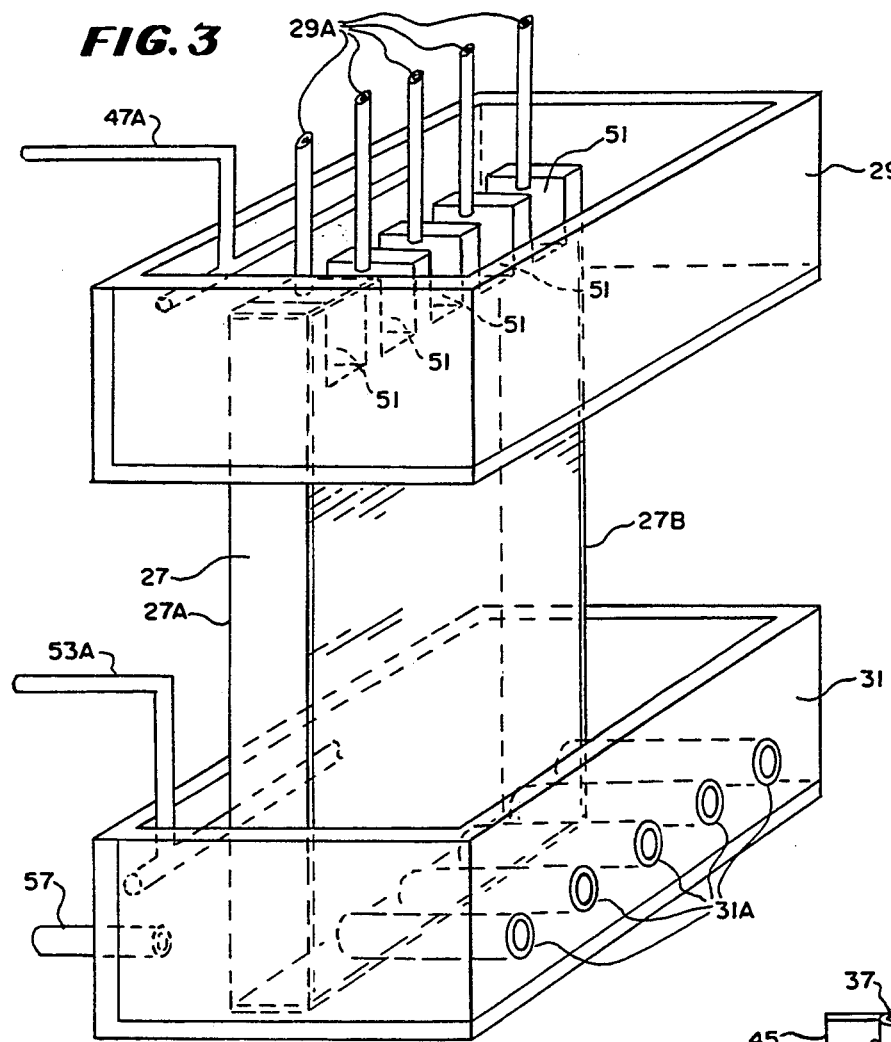
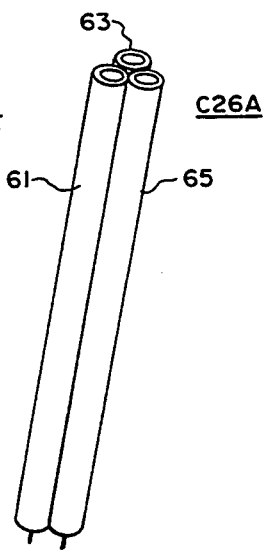
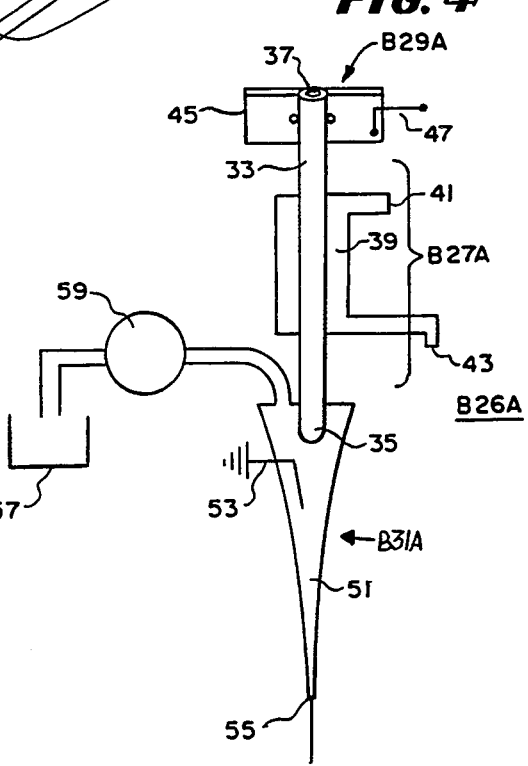

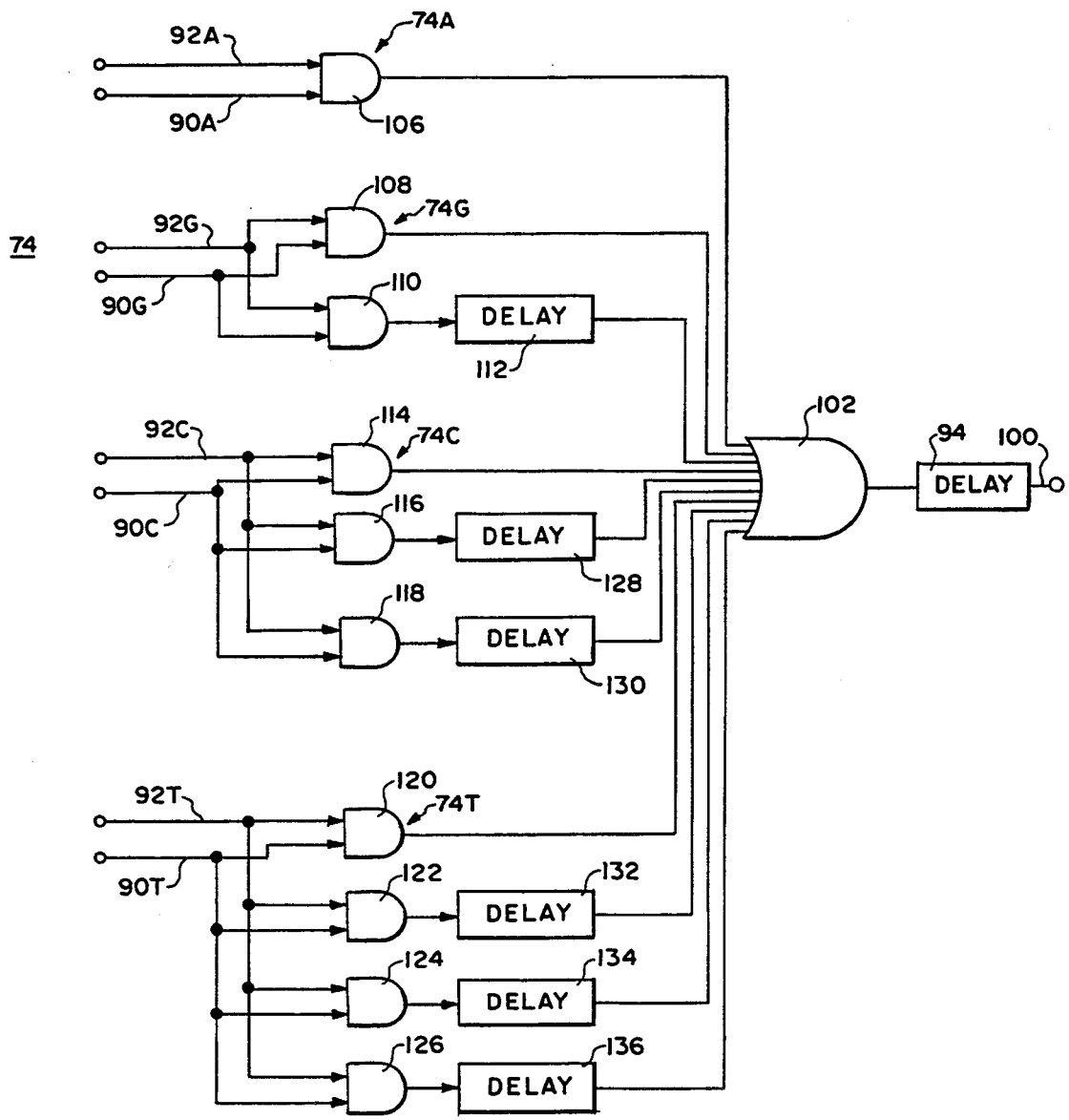

DNA SEQUENCING

This application is a continuation of 07/799,712, filed Nov. 26, 1991 now abandoned; which is a continuation of 07/632,605, filed Dec. 24, 1990 now abandoned; which is a continuation of 07/078,279, filed Jul. 27, 1987 now abandoned; which is a divisional of 06/594,676, filed Mar. 29, 1984 now U.S. Pat. No. 4,729,947.

BACKGROUND OF THE INVENTION

This invention relates to the sequencing of DNA strands.

In one class of techniques for sequencing DNA, identical cloned strands of DNA are marked. The strands are separated into four batches and either individually cleaved at or synthesized to one of the four base types, which are adenine, guanine, cytosine and thymine (hereinafter A, G, C and T). The adenine-, guanine-, cytosine- and thymine- cleaved batches are then electrophoresed for separation. The rate of electrophoresis indicates the DNA sequence.

In a prior art sequencing technique of this class, the DNA strands are marked with a radioactive marker, cleaved at a different base type in each aliquot, and after being separated by electrophoresis, film is exposed to the gel and developed to indicate the sequence of the bands. The range of lengths and resolution of this type of static detection is limited by the size of the apparatus.

In another prior art sequencing technique of this class, single strands are synthesized to a different base type in each aliquot, and the strands are marked radioactively for later detection.

It is also known in the prior art to use fluorescent markers for marking proteins and to pulse the fluorescent markers with light to receive an indication of the presence of a particular protein from the fluorescence.

The prior art techniques for DNA sequencing have several disadvantages such as: (1) they are relatively slow; (2) they are at least partly manual; and (3) they are limited to relatively short strands of DNA.

SUMMARY OF THE INVENTION

Accordingly, it is an object of the invention to provide a novel technique for DNA sequencing.

It is a still further object of the invention to provide novel apparatus and methods for sequencing relatively large chains of DNA.

It is a still further object of the invention to provide apparatus and methods for sequencing cloned DNA fragments of 100 bases or more.

It is a still further object of the invention to provide a technique for continuous sequencing of DNA.

It is a still further object of the invention to continuously sequence DNA without the spatial limitations of range of lengths and resolution.

It is a still further object of the invention to provide a technique for sequencing of DNA.

It is a still further object of the invention to provide a novel technique for continuously sequencing DNA using fluorescent detection.

It is a still further object of the invention to provide a novel technique for DNA sequencing using a fluorescent marker attached to the DNA, or the inherent fluorescence of the DNA itself.

It is a still further object of the invention to provide a novel technique for continuously sequencing DNA marked with fluorescence which more clearly distinguishes marked DNA fragments from background fluorescent noise.

It is a still further object of the invention to provide a novel technique for continuously sequencing DNA using radioactive detection.

In accordance with the above and further objects of the invention, one embodiment of apparatus for sequencing DNA includes at least four electrophoresis channels each adapted to receive cloned DNA strands labeled at one end with biotin and cleaved at the other end at a given type of base. Each of the channels has a gel path and electrical field across it identical in its characteristics to the gel path of the other channels and electrical fields across the other channels.

To provide marking, means are provided for introducing biotin into the DNA fragments prior to their being electrophoresed into the gel with the gel and field being selected so that strands being electrophoresed towards the terminal end of the gel channel are fully resolved prior to the resolution of longer strands towards the beginning of the channel, and so on, in a continuous process over a period of time.

At the terminal end of this separating gel, there is provided means for applying avidin to the strands to further mark the strands individually while maintaining the strands in each channel separate from the strands in other channels. The avidin is pre-marked with multiple fluorescent molecules and therefore provides multiple fluorescent markers for each separated Strand. The application of avidin to the strands may be during further electrophoresing in a second section of the gel, in which unattached avidin is stationary, but the fluorescein- avidin- biotin- DNA complex continues to move.

In another embodiment, strands are synthesized with primers which primers are an inverted complementary sequence. These primers are synthesized by a DNA synthesizer available commercially such as that manufactured by Applied Biosystems. After separation, the inverted complementary sequence forms a hairpin in which ethidium bromide intercalates.

In another embodiment, after separation, ethidium bromide intercalates in duplex DNA formed by palindromes of unprimed DNA or in the single stranded DNA.

In another embodiment, the inherent fluorescence of DNA may be used as a suitable detection mechanism. Thus, it is not necessary to mark one end of the strands with biotin nor mark them with fluorescein nor attach primers with inverted complementary sequences.

In another embodiment, radioactive markers attached directly to DNA may be used as a suitable detection mechanism.

The gel electrophoresis may be provided in conventional gel slabs with input sections for .each of the four channels for A, G, T and C, in addition to any timing that may be needed. As alternatives: (1) four chromatography tubes may be used with gel in them so as to provide more uniform temperature control and eliminate the need for timing channels; (2) open capillary tubes may be used and thus avoid the need for gel and make the cleaning more convenient; or (3) high performance liquid chromatography (HPLC) columns such as ion-exchange columns or reverse phase columns may be used in conjunction with high pressure instead of high voltage for separating the strands within each channel or batch. In using HPLC, sequencing would be performed on smaller strands of DNA called oligonucleotides with typical lengths of 10–50 bases, using one column for each aliquot or at least four.

The detection of the strands is accomplished by moving the strands by bulk flow after electrophoresis or HPLC separation while scanning them with a source of light. Means are provided for detecting the bands individually from each channel in accordance with their time of exit from the gel to indicate the sequence of the A, G, C and T strands of different lengths. Advantageously, an additional channel may be utilized as a calibration channel through the electrophoresis of DNA strands of known, but different lengths. These DNA strands are also marked and thereby indicate a time base.

The scanning apparatus includes a light source, such as a laser or mercury-arc lamp or other suitable source, which emits light in the optimum absorption spectrum of the marker. The light may be split by the use of fiber optics or other conventional optical components, so that there is a source for each of the 4 sample channels as well as any calibration channels.

The detector includes a filtering system for passing selectively the optimum emission band of the fluorescent marker to a light sensor which is preferably a photomultiplier. The photomultiplier or other light controlled mechanism selectively detects the fluorescence using techniques which enhance the signal/noise ratio. One technique is the use of laser pulses which are less than five nanoseconds time duration, with detection in a time window. The length of such window and its delay from the .pulse are optimized to discriminate against background fluorescence. Another technique is to modulate the laser source with an electro-optic modulator, with detection by a lock-in amplifier. There is a detector for each channel, and the combination thereof, indicates: (1) if the type of base termination or nucleotide cleavage is A, G, C or T; and (2) the time of emergence of each strand from each channel of the electrophoresis gel or HPLC column to indicate the overall sequence of strands.

To use the apparatus to sequence DNA strands, cloned strands are normally formed of a length greater than 100 bases. In one embodiment, the strands are marked by biotin at one end. The strands are divided into four aliquots and the strands within each aliquot are cleaved at a different base type. In another embodiment, strands are synthesized to selected base types. These four batches are then electrophoresed through identical channels to separate strands such that the shorter strands are resolved towards the end of the gel prior to resolution of the longer strands, which still are near the beginning of the gel. This occurs in a continuous process so a substantial number of different length strands may be resolved in a relatively short gel. This methodology takes advantage of timeresolved bands, as opposed to the limitations of spatial-resolved bands.

The gel size, electric field and DNA mobilities are such that the first bands to be moved completely through the gel are fully resolved while the last bands are yet unresolved in a continuous process such that at least ten percent of the bands are resolved and electrophoresed through the gel while the lesser mobile bands are yet unresolved near the entrance end of the gel. These lesser mobile bands become resolved little by little over time in a continuous fashion without interruption of the movement of these bands through the gel.

In the one embodiment, near the end of the gel, the biotin terminated fragments are further combined with avidin. The avidin, being a relatively large molecule, may have a plurality of fluorescent markers for each avidin molecule to provide signal amplification. The combination of biotin and avidin may take place either within a second section gel or in liquid after the bands leave the gel.

To attach the avidin within the second section of the gel, the pH of this section may be different from that of the first section. In such a gradient gel the biotin marked strands contact the avidin during electrophoresis. Marked avidin is stationary at a gel pH that is dependent on the number of fluorescein molecules attached to it, whereas DNA is mobile at a gel pH above 4. The electrophoresis of the DNA is done in a first section of the gel having a pH of approximately 7–8, while a band of avidin is located in a second section having its pH in which the fluorescein marked avidin is stationary. In the preferred embodiment, three fluorescein markers are used for each molecule of avidin and the fluoresceinated-avidin has a pI of approximately 8. The avidin should be pure and not contain any DNA or else nonspecific staining may occur. The distance to the second section is sufficiently long enough so that the DNA strands are resolved into bands before reaching the avidin.

The markers are detected by transmitting light in the one embodiment to the fluorescent-avidin-biotin-DNA complexes, in another embodiment to the ethidium-bromide-DNA hairpin complex, and in another embodiment, to an ethidium bromide unmarked DNA complex and in yet another embodiment, to plain DNA, using wavelengths in a narrow wavelength bandwidth in the optimum absorption spectrum of the markers on DNA and detecting emitted fluorescent light either during a time period in which the markers' fluorescence has not yet decayed to an insignificant amount but the background fluorescence has or by modulating the light source and detecting using lock-in techniques. The detection is made in a wavelength band including at least as a principal portion of its energy, the high emission spectrum of the fluorescent marker. For the gated window technique, the light is transmitted from pulsed lasers in approximately three nanosecond pulses. Readings are taken within a window period, after an initial delay, both period and delay are optimized for best results.

In another embodiment, radioactive marked strands, after being separated, are combined with scintillation liquid whereby detection of the presence of the strands is accomplished by an appropriate photodetector.

From the above summary, it can be understood that the sequencing technique of this invention has several advantages, such as: (1) it takes advantage of resolution over time, as opposed to space, (2) it is continuous; (3) it is automatic; (4) it is capable of sequencing relatively long strands including strands of more than 100 bases; and (5) it is relatively economical and easy to use.

SUMMARY OF THE DRAWINGS

The above noted and other features of the invention will be better understood from the following detailed description when considered with reference to the accompaning drawings in which:

FIG. 3 is a simplified schematic of a portion of the embodiment of FIGS. 1 and 2;

FIG. 4 is an alternative embodiment of the portion of FIG. 3;

FIG. 5 is another alternative embodiment of the portion of FIG. 3;

FIG. 8 is a schematic circuit diagram of a portion of the embodiments of FIGS. 1 and 2.

DETAILED DESCRIPTION

Figure 1:
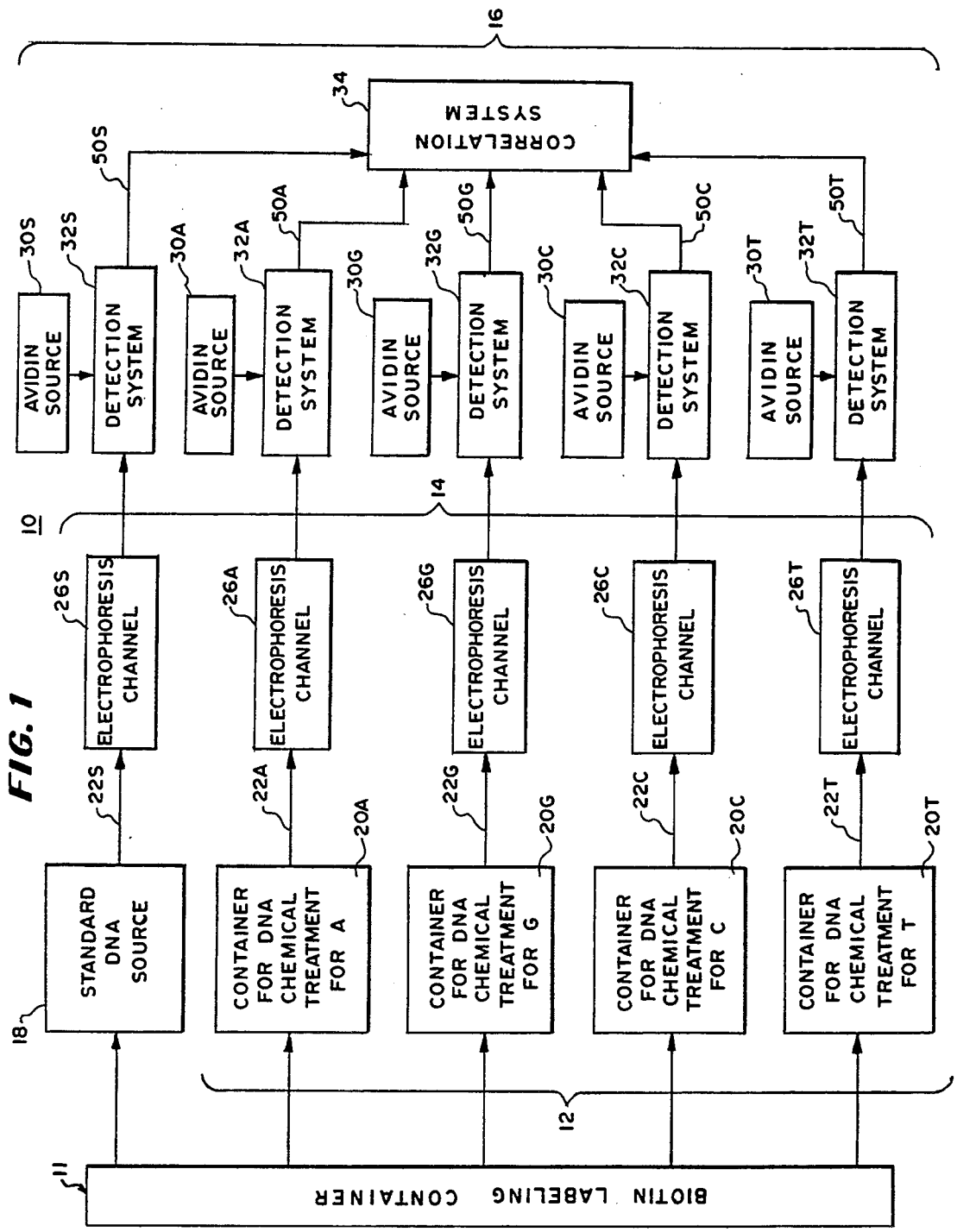
FIG. 1 is a block diagram of an embodiment of the invention.

In FIG. 1, there is shown a block diagram of a DNA sequencing system 10 having a biotin labeling system 11, a DNA cleavage system 12, a separating system 14, a detection and processing system 16 and a source of standard length DNA 18. Biotin labeling takes place before dividing the DNA cloned strands into 4 aliquots.

The biotin from any suitable commercial source is added to the cloned strands of more than 100 bases in a container as indicated at 11. The biotin preparation must be sufficient to mark at least one end of a substantial proportion of the DNA fragments with the biotin in a manner known in the art.

Biotin is selected because of its affinity to avidin and because it is not a large molecule, which in the latter case when added to the DNA fragments might substantially dominate the mobility of the DNA fragments during electrophoresis. Being a small molecule, it does not prevent the discrimination between different DNA fragments within the separating system 14.

Although biotin has been selected as a marker which may be combined later with a larger molecule such as avidin, other markers may be used. They must have characteristics which enable them to be attached to a DNA fragment and to have a strong affinity to a larger molecule which may be marked with a fluorescein or other suitably detectable material. They must also be of such a size and have such chemical characteristics to not obscure the normal differences in the mobilities between the different fragments due to cleavages at different ones of the adenine, guanine, cytosine and thymine bases.

In addition, a radioactive marker such radioactive phosphorus or radioactive sulfur, radioactive carbon or tritium may be incorporated into the DNA molecules such that after separation, strands are combined with scintillation liquid.

The DNA cleavage system 12 communicates in four paths and the source of standard length DNA 18 communicates in one path within the separating system 14 to permit passage of DNA fragments and standard fragments thereto in separate paths. The separating system 14, which sequences strands by separation, communicates with the detection and processing system 16 which analyzes the fragments by comparison with each other and the standard from the source of standard length DNA 18 to derive information about the DNA sequence of the original fragments.

The DNA cleavage system 12 includes four sources 20A, 20G, 20C, 20T of fragments of the same cloned DNA strand. This DNA strand is normally greater than 100 bases in length and is then further cleaved by chemical treatment to provide different lengths of fragments in each of four containers 20A, 20G, 20C and 20T.

In one embodiment, the container 20A contains fragments of DNA strands randomly cleaved by a chemical treatment for A; the container 20G contains fragments of DNA strands randomly cleaved by a chemical treatment for G; container 20C contains fragments of DNA strands randomly cleaved by a chemical treatment for C; and container 20T contains fragments of DNA strands randomly cleaved by a chemical treatment for T. Thus, identical fragments in each container have been cleaved at different bases of a given base type by the appropriate chemical treatment.

The fragments in the containers are respectively referred to as A-DNA fragments, G-DNA fragments, C-DNA fragments and T-DNA fragments from the containers 20A, 20G, 20C and 20T respectively. These fragments are flowed from the containers 20A, 20G, 20C and 20T through corresponding ones of the conduits 22A, 22G, 22C and 22T into contact with the separating system 14.

The source of standard length DNA 18 includes a source of reference DNA fragments of known but different lengths which are flowed through a conduit 22S to the separating system 14. These reference fragments have known lengths and therefore their time of movement through the separating system 14 forms a clock source or timing source as explained hereinafter. While in the preferred embodiment the cloned strands of 100 bases are marked with biotin before being divided into four batches, they may be marked instead after dividing into four batches but before the selected chemical treatment.

The separating system 14 includes five electrophoresis channels 26S, 26A, 26G, 26C and 26T. The electrophoresis channels 26S, 26A, 26G, 26C and 26T include in the preferred embodiment, gel electrophoresis apparatus with each path length of gel being identical and having the same field applied across it to move samples continuously through five channels. The gels and fields are selected to provide a mobility to DNA strands that does not differ from channel to channel by more than 5% in velocity. In addition, the field may be varied over time to enhance the speed of larger molecules after smaller molecules have been detected, as well as to adjust the velocities in each channel based on feedback from the clock channel to compensate for differences in each channel such that the mobilities in each channel are within the accuracy required to maintain synchronism among the channels.

Preferably the gels are of the same materials, chemical derivatives and lengths and the electric fields are within 5% of the intermediates of each other in each channel. However, more than one reference channel can be used such that a reference channel is adjacent to a sample channel in order to minimize the requirements for uniformity of DNA movement in the gel for all channels.

The electrophoresis channel 26S receives fragments of known length DNA marked with biotin and moves them through the gel. Similarly, each of the electrophoresis channels 26A, 26G, 26C and 26T receives biotin-labeled fragments from the cleavage system 20A, 20G, 20C and 20T and moves them in sequence through the sample electrophoresis channels, with each being moved in accordance with its mobility under a field identical to that of the reference electrophoresis channel 26S.

To provide information concerning the DNA sequence, the detection and processing system 16 includes five avidin sources 30S, 30A, 30G, 30C and 30T; five detection systems 32S, 32A, 32G, 32C and 32T and a correlation system 34. Each of the avidin sources 30S, 30A, 30G, 30C and 30T is connected to the detecting systems 32S, 32A, 32G, 32C and 32T. Each of the outputs from corresponding ones of the electrophoresis channels 26S, 26A, 26G, 26C and 26T within the separating system 14 is connected to a corresponding one of the detection systems 32S, 32A, 32G, 32C and 32T. In the detection system, avidin with .fluorescent markers attached and DNA fragments are combined to provide avidin marked DNA fragments with fluorescent markers attached to the avidin to a sample volume within the detection system for the detection of bands indicating the presence or absence of the fragments, which over time relates to their length.

The output from each of the detection systems 32S, 32A, 32G, 32C and 32T are electrically connected through conductors to the correlation system 34 which may be a microprocessor system for correlating the information from each of the detection systems to provide information concerning the DNA sequence.

The avidin sources 30S, 30A, 30G, 30C and 30T each contain avidin purchased from known suppliers, with each avidin molecule in the preferred embodiment combined with three fluorescein moleules. The avidin sources are arranged to contact the DNA fragments and may be in a section of gel placed adjacent to the electrophoresis channel. In this use, this section of the gel should have a pH of approximately 8 to avoid movement of the three fluorescein-marked avidin by electrophoresis. When the biotinylated DNA strands reach the section of gel that has a pH of 8, they will pick up the fluoresceinated avidin which moves very slowly or is stationary in this section of the gel.

To prepare the second section of gel with fluoresceinated avidin, the fluoresceinated avidin may be electrophoresed from the exit end of the channel inwardly. In this embodiment, it moves in this direction slowly because its pI is slightly higher than the pH of the second section of gel. Alternatively, it may be mixed in gel.

Because the fluorescein-avidin-biotin-DNA complex molecule is acidic in the pH 8 gel, it will continue to move out of this section of the gel where it is then passed to a sample volume within the detection system by an eluant. The sequences of separation determined before the attachment of avidin are maintained and not substantially altered. In the alternative, the bands of DNA fragments may be electrophoresed into a more mobile liquid containing fluorescein marked avidin for combination with the avidin. The avidin binds selectively to the biotin attached to the ends of the DNA fragments and unreacted fluoresceinated avidin is separated from the fluorescein-avidin-biotin-DNA complex by standard techniques such as chromatography.

The detection systems each include an optical system for detecting the presence or absence of bands and converting the detection of them to electrical signals which are applied electrically to the correlation system 34 indicating the sequence of the fragments with respect to both the standard fragments from the source of standard length DNA 18 and the A, G, C and T fragments from the containers 20A, 20G, 20C and 20T respectively.

Figure 2:
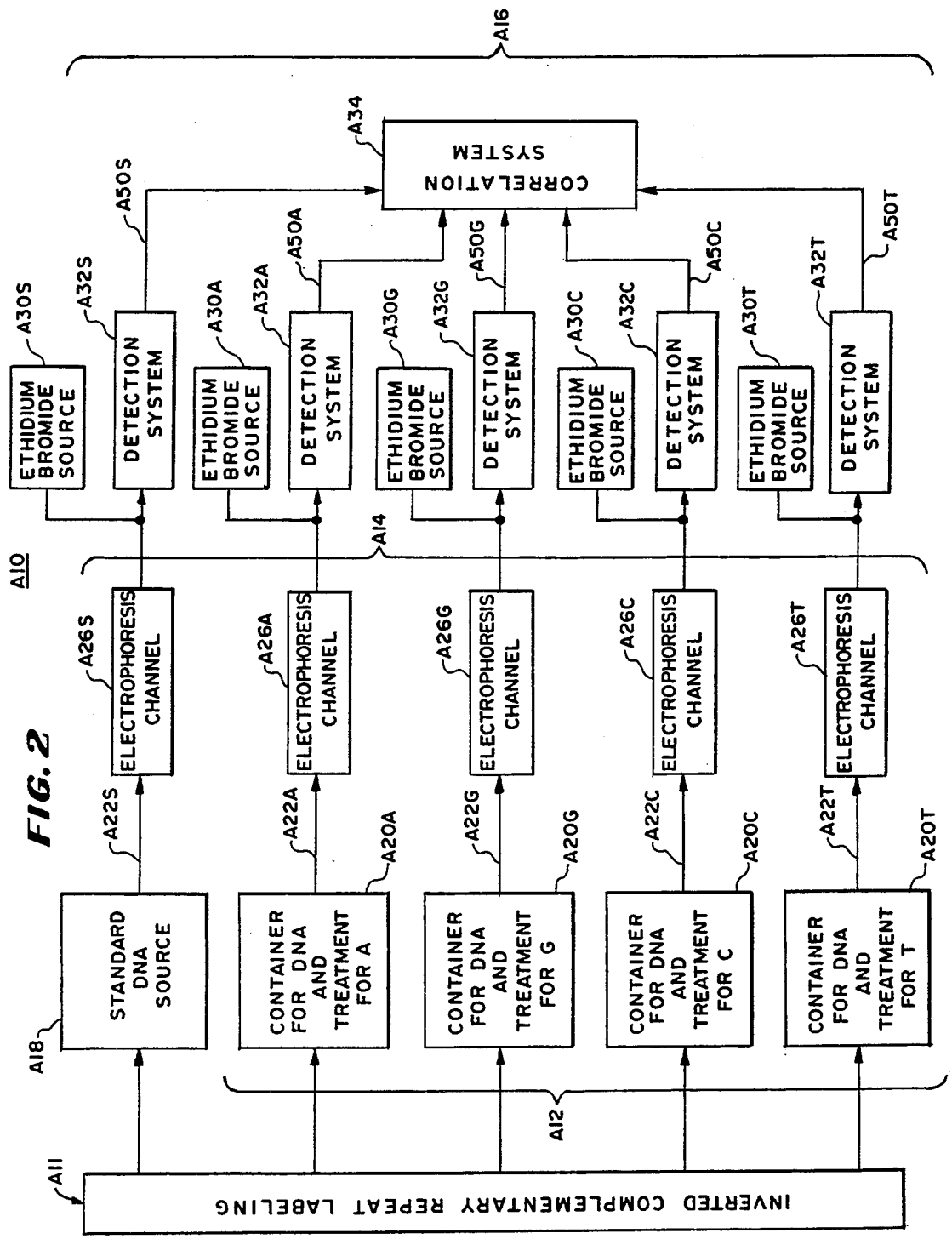
FIG. 2 is a block diagram of another embodiment of the invention.

In FIG. 2, there is shown a simplified block diagram of another embodiment of DNA sequencing apparatus A10. This apparatus is similar to the DNA sequencing apparatus 10 of FIG. 1 and the components are identified in a similar manner with the reference numbers being prefixed by the letter A.

In this embodiment, instead of the containers for DNA and chemical treatment for A, G, C and T of the embodiment of DNA sequencing system 10 shown at 20A, 20G, 20C and 20T in FIG. 1, the DNA sequencing apparatus A10 includes containers for treatment of the DNA in accordance with the method of Sanger described by F. Sanger, S. Nicklen and A. R. Coulson, "DNA Sequencing with Chain-Terminating Inhibiters," *Proceedings of the National Academy of Science, USA*, Vol. 74, No. 12, 5463–5467, 1977, the disclosure of which is incorporated herein, indicated in the embodiment A10 of FIG. 2 at A20A, A20G, A20C and A20T shown as a group generally at A12.

In this method, the strands are separated and used as templates to synthesize DNA with synthesis terminating at given base types A, G, C or T in a random manner so as to obtain a plurality of different molecular weight strands. The limited synthesis is obtained by using nucleotides which will terminate synthesis and is performed in separate containers, one of which has the special A nucleotide, another the special G nucleotide, another the special C nucleotide and another the special T nucleotide. These special nucleotides may be dideoxy nucleotides or marked nucleotides, both of which would terminate synthesis. So, each of the four batches will be terminated at a different one of the types of bases A, G, C and T randomly.

In this embodiment, the fragments may be marked by biotin at one end in the manner shown in FIG. 1. However, in the preferred embodiment of FIG. 2, instead of labeling with biotin, the fragments are labeled by an inverted complementary repeat of DNA as shown at A11 before being applied to the channels indicated at A12 in FIG. 2. The design of inverted complementary repeat takes advantage of the process of designing small DNA fragments known as oligonucleotides. This process is widely described in the literature as well as such patents as Phosphoramidite Components and Processes (U.S. Pat. No. 4,415,732), the disclosure of which is incorporated herein.

After the electrophoresis, the inverted complementary repeat forms a hairpin from a palindrome of duplex DNA, which is then combined with ethidium bromide and detected by the detection system using a wavelength of light appropriate to the intercalated ethidium bromide rather than wavelengths of light appropriate to the fluorescein marking. If one uses highly sensitive detection techniques, the inverted repeat would not be used and detection would be accomplished either by sensing ethidium bromide that intercalated between portions of the unknown DNA that happened to form duplex DNA, or by ethidium bromide that attached to single stranded DNA, or by the inherent fluorescence of the DNA itself. If one used radioactive markers, detection would be accomplished by sensing light given off by the combination of the radioactive marker and scintillation fluid.

In FIG. 3, there is shown one type of separating system which includes a slab of gel 27 as known in the art with five sample dispensing tubes indicated generally at 29A terminating in aligned slots 51 in the gel 27 on one end, with such slots in contact with a negative potential buffer well 29 having a negative electrode 47A, and five exit tubes at the other end located at 31A terminating in apertures in the gel 27, as well as a positive potential buffer well 31 having a positive electrode 53A. The material to be electrophoresed is inserted into slots 51 through tubes 29A and due to the field across the gel 27 moves from top to bottom in the gel and into the appropriate corresponding exit tubes of the group 31A. The gel slab 27 has glass plates 27A and 27B on either side to confine the sample and gel. Buffer fluid from the buffer well 31 is pumped at right angles to the gel 27 from a source at 57 by pumps connected to tubes 31A to pull fluid therethrough. The buffer fluid picks up any DNA that is electrophoresed into the exit holes 31A and makes its way to sensing equipment to be described hereinafter or to provide communication with other gel slabs for further electrophoresis of the DNA strands being electrophoresed from the slab 27.

In FIG. 4, there is shown another embodiment B26A of gel electrophoresis having a negative-potential buffer for the A channel indicated generally at B29A, a gel electrophoresis channel for A terminated DNA indicated at B27A and a positive potential buffer for the channel indicated at B31A. This embodiment is intended to provide a thin cylindrical gel for each channel so as to permit easier temperature control and thus alleviate changes in migration rates by different temperatures such as may occur across the slab 27 (FIG. 3). In addition, the field could be adjusted independently for each channel to maintain proper synchronization.

For this purpose, the Channel B27A includes a 0.5 to a 1 millimeter inner diameter pyrex column such as a chromatographic column indicated at 33 with a gel inside of it. The gel is prepared by inserting it in the column while unhardened and permitting it to harden. The column 33 is of sufficient length to separate the DNA. Fluoresceinated avidin may be initially electrophoresed upward from its exit end shown at 35 to meet with DNA entering from its entrance end shown at 37 in the embodiment which uses biotin-avidin-fluorescein as a marker. The column may be temperature controlled by a conventional chromatographic temperature controlling apparatus 39 which is a glass casing about the column which receives a liquid at one end such as at 41 and removes it at 43.

At one end of the channel B27A is the buffer B29A adapted to provide a buffer solution in a plexiglas surrounding cup shaped container 45, which buffer extends over the entering end 37 and contains within it a negative voltage electrode 47.

At the exit end, there is similarly mounted a buffer compartment 51 containing buffer which is grounded by an electrode 53 and emerses in buffer the exit end 35 of the gel column B27A. It may be made of plexiglass and may be shaped with a reducing orifice ending in a micro-orifice 55 at its lower end to permit the flow of buffer therethrough containing DNA which emerged from exit end 35 for detecting with a chopped light source as described above. To supply new buffer, a buffer reservoir 57 is connected through a pump 59 to the top of the buffer 51, with the flow rates being designed to prevent a vortex near the exit end 35 and to permit a flow rate sufficient for optimum signal-to-noise ratio of buffer. Another embodiment would transfer the flowing buffer-DNA solution to a flow-through cell for detection in a spectrofluorometer or specifically designed HPLC fluorescence detection.

In one embodiment, the buffer may include the ethidium bromide for exciting 300 or 390 nanometers and detecting at 590 nanometers.

In FIG. 5, there is Shown still another embodiment C26A which may be substituted for the column 33 and gel and includes capillary columns 61, 63 and 65 as commonly used in capillary electrophoresis. These columns may be filled with buffer solution rather than a gel and be used for electrophoresis. In such a case, several capillaries may be used as a substitute for one column of the embodiment of FIG. 4. Thus, the same band of A, G, C or T type bases might flow through several parallel bundles of capillaries, or they might flow through only one capillary per type of base.

The separation path such as gel channels or capillary tube length should be no longer than two meters for a range of lengths of DNA from 50 to 10,000 or more bases. However, as the range of DNA lengths increase, the time required increases. Also, the time required for each separation is in the range of from $\frac{1}{2}$ second to 5 minutes for each added base of length separation.

Figure 6:
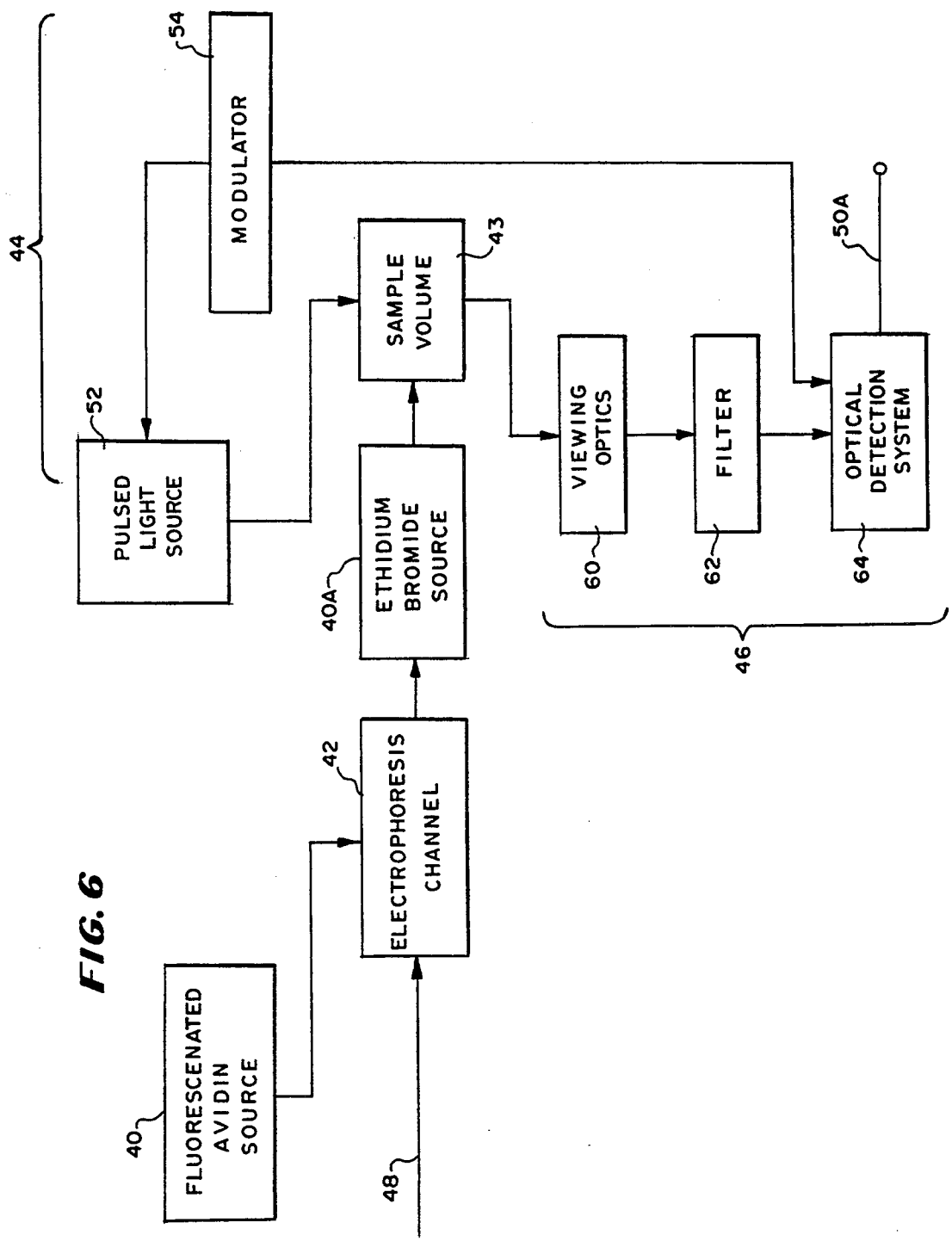
FIG. 6 is a block diagram of a portion of the embodiments of FIGS. 1 and 2.

In FIG. 6 there is shown a block diagram of the detection system 32A. The detection systems 32S, 32G, 32C and 32T are substantially identical to the detection system 32A and so only the system 32A will be described in detail herein. The detection system 32A includes an electrophoresis channel 42, a sample volume 43, a light source 44 and an optical detection system 46.

In one embodiment avidin marked with fluorescein in the fluoresceinated-avidin source flows into the gel which receives A type terminated strands from channel 26A on conduit 48 and is attached to the biotinylated DNA fragments. Actually, the electrophoresis channel 42 may be a gel section positioned at the end of the electrophoresis channel 26A for continuous electrophoresing. After the fluoresceinated avidin is attached to the biotinylated DNA in the electrophoresis channel 42, the complex molecule is eluted out of the electrophoresis channel 42 into the sample volume.

In another embodiment, the DNA may be marked by a palindrome described above and the detection system would then utilize a different wavelength of light and would not require the fluorescenated-avidin source 40 but rather an ethidium bromide source 40A.

The sample volume 43 is irradiated by the light source 44. Light from the light source 44 is detected and converted to electrical signals by the optical detection system 64 for application through the conductor 50A to the correlation system 34 (FIG. 1). In one embodiment, the fluorescenated-avidin source 40 contains a fluorescent marker having a period of fluorescence sufficiently long compared to background fluorescence in the DNA and associated materials to permit significant separation of the signal from the fluorescence. In this embodiment, the decay lifetime of the fluorescent marker should be at least ten times the duration of the background fluorescence which background fluorescence is expressed in the form of noise in a detected signal.

Some known appropriate fluorescent markers are: (1) rare-earth organo complexes, consisting of rare earth bound to organic compounds with the resulting complex having the desired properties, such as europium, benzoylacetonate and europium benzoyltrifluoroacetonate, as discussed by S. I. Weissman in the *Journal of Chemical Physics,* vol. 10, page 214–217, 1942 incorporated by reference herein; (2) pyrenebuterate, as discussed by Knopp and Weber in the *Journal of Biological Chemistry,* vol. 242, p. 1353 (1963) and vol. 244, p. 3609 (1969) incorporated by reference herein; (3) fluorescein isothiocyanate (FITC); (4) rhodamine isothiocyanate (RITC); (5) tetramethylrhodamine isothiocyanate (TRITC); (6) phycoerythrin; and (7) their analogs and substituted derivatives. Such materials are available commercially such as from Research Organics in Cleveland, Ohio. In the preferred embodiment, fluorescein avidin DCS is purchased from Vector Laboratories, Inc., 1429 Rollins Road, Burlingame, Calif. 94010.

The light source 44 includes a pulsed light source 52 and a modulator 54. The pulsed light source 52 is selected to emit light within the absorbance spectrum of the fluorescent marker. Since different fluorescent markers may be used, this frequency differs from fluorescent marker to fluorescent marker. Moreover, in one embodiment, the modulator 54 controls the pulsed light source 52 to select intervals between pulses, the intervals being provided to permit the decay of fluorescent light from the background fluorescent material, during which time the fluorescent light from the bound markers is measured.

These time periods between pulses are sufficiently long to encompass the entire delay period. This is done because the delay period of the attached fluorescent marker is relatively long compared to background noise fluorescence and so a period of time may pass before the measurement is made by the optical detection system 46. Typically, the pulse of light has a duration of approximately three nanoseconds and the background fluorescence decay lasts for approximately ten nanoseconds while the fluorescent marker attached to the avidin has a decay lifetime of 100 nanoseconds.

Typically, the optical detection system 46 begins reading at approximately 50 nanoseconds after the initiation of the excitation pulse from the laser and continues for approximately 150 nanoseconds until 200 nanoseconds after the initiation of the three nanosecond pulse. Although in the preferred embodiment, a pulsed laser light source 52 is utilized, a broad band light source combined with filters or a monochrometer may be utilized to provide the narrow band in the absorption spectrum of the marker.

Another embodiment uses an electro-optic modulator which modulates a continuous light source at a frequency typically at 10 khz, with essentially 100% depth of modulation and 50% duty cycle. A pulse generator provides a signal both to the modulator via a driver and to a lock-in amplifier as a reference signal. Another embodiment uses a continuous light source with no modulations.

To detect the bands in the electrophoresis gel of the electrophoresis channel 42 indicating particular DNA fragments, the optical detection system 46 includes viewing optics 60, a filter 62, and an optical detection system 64. The filter 62 selects the frequency of light transmitted through it by the viewing optics 60 which focuses the light onto the optical detection system 64. The optical detection system 64 is electrically connected to the modulator 54 to gate an electrical signal to the conductor 50A indicating the presence or absence of a band of DNA fragments in the electrophoresis channel 42.

The filter 62 in the preferred embodiment includes an interference filter having a pass band corresponding to the high emission spectrum of the fluorescent marker. Such filters are known in the art and may be purchased from commercial sources with bands to correspond to common emission bands of fluorescent markers. In addition, there may be long-wavelength-passing interference filters and/or colored glass filters. Another embodiment uses a monochrometer instead of a filter.

The viewing optics 60 consists of a lens system positioned in juxtaposition with filter 62 to focus light onto the optical detection system 64. It may be any conventional optical system, and the optical detection system 64 should include a semiconductor detector or a photomultiplier tube, such as the Model EMI 9798A made by EMI Gencon, Plainview, N.Y.

In the first embodiment, the output of the photomultiplier or semiconductor is gated in response to the signals from the modulator 54 to occur after a time delay after each pulse from the pulsed laser light source 52. For example, a time delay may be included before the electrical signal is applied to an amplifier and thus provide an electrical signal to the conductor 50A or to an amplifier, the output of which is electrically connected to the conductor 50A. In the preferred embodiment, the time delay is 50 microseconds and the gate or amplifier is maintained open by a monostable multivibrator for approximately 150 nanoseconds. In the second embodiment, the square wave output of a modulator is compared with the signal from the detector using a lock-in amplifier. In a third embodiment, no modulation is performed.

Figure 7:
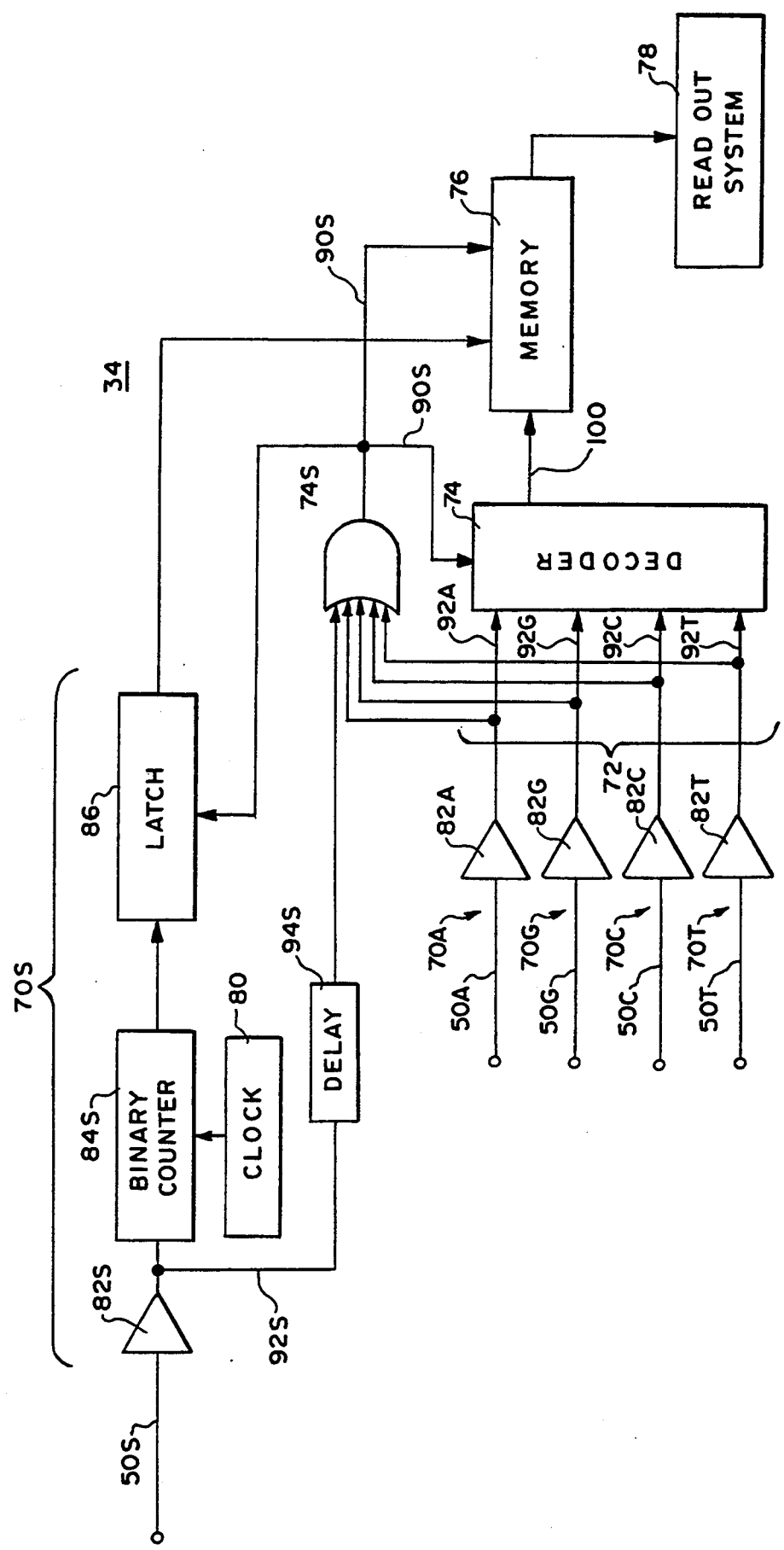
FIG. 7 is a logical circuit diagram of a portion of the block diagram of FIG. 3.

In FIG. 7 there is shown a block diagram of the correlation system 34 having a standard channel input circuit 70S, a gating system 72, a decoder 74, a memory 76 and a read-out system 78. The standard channel input circuit 70S is electrically connected to the OR gate 74S which is electrically connected to the other channels A, G, C and T and to the gating system 72 which receives channel input signals from each of the channels A, G, C, and T similar to that of channel 70S.

The gate 74S is electrically connected to the memory 76 which receive signals from gate 74S indicating the presence of DNA fragments in the particular one of the nucleic acid bases or in the standard channel. The memory 76 is electrically connected to the read-out system 78 to print out the sequence.

The standard channel input circuit 70S includes a pulse shaper 82A, a binary counter 84S, a time delay 94S of the clock 80 and a latch 86 with the input of the pulse shaper 82S being electrically connected to a conductor 50S and its output being connected to OR gate 74S through time delay 94S and to the binary counter 84S. The output of the binary counter 84S is connected to the latch 86 to provide a time increment signal to the latch 86, the output of which is applied to one of the inputs of memory 76 when triggered by a signal from OR gate 74S. The conductor 50S corresponds to conductors 50A, 50G, 50C and 50T (FIG. 2) except that conductor 50S is the output for the standard clock channel rather than for adenine, quanine, cytosine or thymine.

The latch 86 and the decoder 74 are pulsed by a signal from the gate 74S to write into the memory 76 for recording with a distinctive signal indicating a clock timing pulse which is later printed to indicate the time that particular DNA segments have been received and detected in the detection system 32A, 32G, 32C and 32T (FIG. 1). The binary counter 84S receives clock pulses from clock 80 to which it is connected and thus contains a binary signal representing time for application to the latch 86.

The switching circuit 72 includes a decoder 74 which is electrically connected to four inputs from channels 70A, 70G, 70C and 70T respectively, for receiving signals indicating the presence of types A, G, C, and T, fragments as they appear on input conductors 50A, 50G, 50C and 50T, (of FIG. 1 and FIG. 2). The signals on conductors 50A, 50G, 50C, and 50T are each applied to respective ones of the pulse shapers 82A, 82G, 82C, and 82T, the outputs of which are electrically connected through corresponding ones of the conductors 92A, 92G, 92C, and 92T to different inputs of the decoder 74 and to inputs of the OR gate 74S, so that the decoder 74 receives signals indicating the presence of a DNA fragment for application to the memory 76 upon receiving a signal on conductor 90S from the OR gate 74S. The OR gate 74S applies such a signal when receiving a calibration signal from the channel 70S or when receiving a signal from any one of the channels 70A, 70G, 70C, and 70T, so that the memory 96 receives calibration signals or signals indicating DNA for reading out, after a delay within the memory 76, to the readout system 78.

The OR gate 74S receives its calibration signal from channel 70S after a delay imparted in the delay line 74S, but does not have such a corresponding delay in channel 70A, 70G, 70C, and 70T. However, a similar delay is within encoder 74 to be described hereinafter so that the appearance of DNA fragments will be sent to the memory 76 in a time frame corresponding to that of the calibration signals from channel 70S. The output of the decoder 74 is electrically connected to the memory 76 through a conductor 100.

In FIG. 8, there is shown a schematic circuit diagram of the decoder 74 having a delay line 94, an OR gate 102 and a plurality of coding channels 74A, 74G, 74C and 74T to respectively indicate fragments terminating with the bases, adenine, guanine, cytosine and thymine respectively.

The channel 74A includes AND gate 106, having its inputs electrically connected to conductor 92A and 90A to receive on conductor 90A a clock signal from the OR gate 74S (FIG. 7) and on its other input a signal indicating the presence of an adenine terminated fragment on conductor 92A.

Channel 74G includes AND gate 108, AND gate 110 and delay line 112. Conductor 92G indicating a guanine terminated strand is electrically connected to the inputs of AND gate 108 and 110. The output of AND gate 108 is connected to one of the inputs of OR gate 102 and the output of AND gate 110 is electrically connected through delay line 112 to the input of OR gate 102 to provide two pulses in succession to gate 102. Thus, channel 74A applies one out pulse from the output of AND gate 106 to one of the inputs of OR gate 102, whereas channel 74G applies two pulses. In either case, the sequence of pulses indicates the presence of a particular one of the types of DNA fragments A or G.

Similarly, the channel 74C includes AND gates 114, 116 and 118, each having one of its two inputs electrically connected to conductor 92C and 90C and the channel 74T includes AND gates 120, 122, 124 and 126, each having one of its inputs electrically connected to conductor 92T and the other connected to 90T. The output from an AND gate 74C is electrically connected to an input of OR gate 102, the output of AND gate 116 is electrically connected through a delay 128 to the input of OR gate 102, and the output of AND gate 118 is electrically connected through a delay 130 longer than the delay 128 to an input of the OR gate 106. With this arrangement, the presence of a DNA strand terminating with cytosine results in three pulses to the 0R gate 102.

The output of AND gate 120 is electrically connected to an input of the OR gate 102, the output of the AND gate 122 is electrically connected through a delay 132 to an input of the OR gate 102, the output of AND gate 124 is electrically connected through a delay 134 longer than the delay 132 to an input of the OR gate 102 and the output of AND gate 126 is electrically connected through a delay 136 longer than the delay 134 to an input of the OR gate 102. In this manner, the presence of a thymine-terminated fragment results in four signals in series to the inputs of OR gate 102. The out gate of OR gate 102 is applied through a delay 94 with a similar time delay as the delay 94S (FIG. 7) to the output conductor 100 so as to provide a coded signal indicating the presence of a particular DNA group to the memory 76 (FIG. 7) coordinated with a time signal.

In the operation of sequencing DNA, DNA strands with bases above 100 in number are first marked with biotin, separated in accordance to the size of the fragment and then marked with avidin marked with one or more fluorescent molecules. The bands are then detected by light with the read-out in the emission spectrum taking place a sufficient amount of time after excitation in the emission spectrum to screen against noise.

To mark DNA fragments with biotin, cloned strands are prepared and cleaved into fragments after which they are first marked with biotin and then divided into four aliquots. A standard source of DNA strands also marked with biotin and having different rates of migration under electrophoresis forms additional calibration batches. The four batches are each individually, randomly cleaved by a chemical treatment for a different one of adenine, guanine, cytosine and thymine bases. In the alternative, strands may be separated and used as templates for synthesizing randomly to a selected base type. In either case, the strands may be marked with biotin, marked with an inverted complementary sequence of DNA, marked with a radioactive marker or left unmarked.

To separate the fragments, the biotin marked fragments including any standard ladder source are each individually electrophoresced through gel in different channels or in different columns. The gel and the field must be uniform, although reference channels reduce uniformity requirements, and when a single slab is used to migrate several different samples, the channels must be kept separate and be centered sufficiently around the field so that the potential for causing them to migrate is uniform. Preferably, the pH of the gel for separation is 7.5-8.

The DNA fragments separate in accordance with their length during electrophoresis. Thus, the fastest migrating fraction is the fragment which is cut or synthesized to the first base closest to the marked end of the strand and, since the channels are separate, it is known which base A, G, C or T is the first one in the sequence from the channel.

The next band in time in the gel is the next cleavage point which is one base longer than the first one since it encompasses both the first base and the second one from the biotinylated end of the DNA strand. Similarly, the third fragment to form a band during electrophoresis will encompass the first three base units and so on.

Because a large number of bases are used, there is a larger number of cleavage points and the density of fragments in each band is relatively low. Thus, the gel and the field must be selected to provide a band of sufficient width, high enough density and adequate separation for detection. The gel slab is sufficiently long such that the first bands to be moved completely through the gel are fully resolved while the last bands are unresolved in a continuous process. More specifically, at least 10 percent of the bands are resolved and electrophoresed through the gel while the least mobile bands are yet unresolved near the entrance end of the gel.

To provide light amplification for measurement of the low density bands in one embodiment, the bands are electrophoresced into a region where they are mixed with avidin marked with one or more fluorescent molecules. Because avidin is a large molecule and strongly attracted to the biotin, the DNA fragments in each band, as they are moved into a fluorescent-marked avidin region, are marked with avidin. After being marked with avidin such as indicated at 32S, 32A, 32G, 32C and 32T (FIG. 1), they are each moved through a detection system such as the one illustrated in FIG. 2.

Because the avidin molecules are large, a number of fluorescent markers are attached to the same avidin molecule thus providing adequate detection. The fluorescent-marked fragments are then moved into the sample volume within the detection system where they maintain their relative order. The movement must be sufficiently rapid in the gel so that minimum resolution is lost.

The bands are eluted into the sample volume where individual light sources apply pulsed or chopped light within the optimum absorption spectrum of the fluorescent marker or ethidium bromide marker in the second embodiment of approximately three nanoseconds duration. The light is sensed by a detector approximately fifty nanoseconds after the beginning of the three nanosecond pulse of light and the resulting electrical signal is amplified. This light is detected and correlated to provide the sequence of DNA in accordance with the channel as indicated by a detector at the end of each of the detection systems.

As can be understood from the above description, the DNA sequencing system of this invention enables continuous sequencing and thus may handle in a continuous, automatic manner, a large number of bases. This is accomplished by the combination of continuous electrophorescing with the amplification provided by the avidin attachment at the end of the first separation.

Although a preferred embodiment of the invention has been described with some particularity, many modifications and variations are possible in the preferred embodiment within the light of the above description. Accordingly, within the scope of the appended claims, the invention may be practiced other than as specifically described.

What is claimed is:

1. Apparatus comprising:
   separating apparatus;
   said separating apparatus having at least four identical gel electrophoresis channels and at least four separate channel-introducing sections each of which corresponds to a different one of said at least four identical gel electrophoresis channels, wherein each of said four identical channel-introducing sections is adapted to receive DNA fragments terminated at different ones of four nucleic acid molecules, A, G, C and T;
   means establishing potential across said at least four identical gel electrophoresis channels and at least four separate channel-introducing sections, wherein bands of more mobile DNA fragments are fully resolved in the gel electrophoresis channels while some of the less mobile strands to be later formed into bands are unresolved in a continuous process;
   said separating apparatus including means for maintaining four separate groups of DNA fragments in accordance with the terminating base;
   means for marking said DNA fragments prior to their entrance into the electrophoresis gel with biotin;
   means for attaching a flourescent marker to avidin;
   means for marking said DNA fragments after they have been electrophoresed through said electrophoresis apparatus with fluorescenated avidin;
   means for selectively pulsing said markers with light;
   means for detecting the fluorescence of said marker across a time period in which background fluorescence is reduced; and
   said means for detecting including means for converting said fluorescence into electrical signals indicating the time sequence of bands of DNA marked with fluorescence corresponding to each of the DNA fragments cleaved at different ones of the nucleic acid groups.

2. Apparatus comprising:
   gel electrophoresis apparatus;
   said gel electrophoresis apparatus having at least four separate channel-introducing sections each adapted to receive DNA fragments cleaved at different ones of four nucleic acid molecules, A, G, C and T;
   means for establishing potential across said gel electrophoresis apparatus wherein bands of more mobile DNA fragments are fully resolved at the end of said gel electrophoresis apparatus while some of the less mobile strands to be later resolved into bands are unresolved in a continuous process;
   means for marking said DNA fragments prior to their entrance into the electrophoresis gel with biotin;
   said gel electrophoresis apparatus including means for maintaining four separate groups of DNA fragments in accordance with the nucleic acid molecule at which they were cleaved;
   means for marking said DNA fragments after they have been electrophoresed through said electrophoresis apparatus with avidin; and
   means for attaching a fluorescent marker to said avidin.

3. Apparatus according to claim 2 further including:
   means for selectively pulsing said markers with light;
   means for detecting the fluorescence of said markers across a time period in which background fluorescence is reduced; and
   said means for detecting including means for converting said fluorescence into electrical signals indicating the time sequence of bands of DNA marked with fluorescence corresponding to each of the DNA fragments cleaved at different ones of the nucleic acid groups.

4. Apparatus comprising:
   gel electrophoresis apparatus;
   said gel electrophoresis apparatus including at least four separate tubes each adapted to receive DNA fragments terminated at different ones of four bases, A, G, C and T;
   means for establishing a potential across said tubes wherein bands of the DNA fragments are fully resolved at the end of said electrophoresis apparatus prior to the resolution of the last to be introduced bands;
   means for marking said DNA fragments prior to their entrance into the electrophoresis gel with biotin;

said gel electrophoresis apparatus including means for maintaining four separate groups of DNA fragments in accordance with the nucleic acid molecule at which they were cleaved;

means for marking said DNA fragments after they have been electrophoresed through said electrophoresis apparatus with avidin; and means for attaching a fluorescent marker to said avidin.

5. Apparatus for sequencing DNA comprising:

means for applying fluorescently marked DNA strands with random lengths terminated at least at one of different ones of adenine bases, guanine bases, cytosine bases and thymine bases to at least one channel of a separating apparatus, wherein at least one batch of DNA strands is formed, which batch is terminated at one of the adenine bases, guanine bases, cytosine bases and thymine bases;

means for electrophoresing the fluorescently marked DNA strands in said at least one channel of the separating apparatus, wherein the strands are separated within at least one channel so that the bands of more mobile strands in the at least one channel are fully resolved while some of the less mobile strands to be later formed into bands are unresolved in a continuous process such that at least ten percent of the bands are fully resolved while the less mobile strands are yet unresolved into bands in the at least one channel;

means for applying light from a source of light to the resolved bands; and means for identifying and recording the sequence of the bands in the at least one channel from the reaction of the fluorescently marked strands with the light to indicate the DNA sequence.

6. Apparatus according to claim 5 in which said means for applying light includes means for scanning strands with a source of light.

* * * * *